United States Patent
Lo et al.

(10) Patent No.: US 8,862,213 B2
(45) Date of Patent: Oct. 14, 2014

(54) SYSTEM AND METHOD FOR IMPROVED COMPLEX FRACTIONATED ELECTROGRAM ABLATION

(75) Inventors: Men-Tzung Lo, Jhongli (TW); Yenn-Jiang Lin, Taipei (TW); Shih-Ann Chen, Taipei (TW); Yi-Chung Chang, Jhongli (TW); Chen Lin, Jhongli (TW); Ke-Hsin Hsu, Jhongli (TW); Wan-Hsin Hsieh, Jhongli (TW); Hung-Yi Lee, Jhongli (TW); Norden E. Huang, Jhongli (TW)

(73) Assignee: National Central University, Jhongli (TW)

( * ) Notice: Subject to any disclaimer, the term of this patent is extended or adjusted under 35 U.S.C. 154(b) by 148 days.

(21) Appl. No.: 13/558,616

(22) Filed: Jul. 26, 2012

(65) Prior Publication Data
US 2014/0031708 A1    Jan. 30, 2014

(51) Int. Cl.
*A61B 5/046*    (2006.01)

(52) U.S. Cl.
USPC ............ 600/518; 600/508; 600/509; 600/515

(58) Field of Classification Search
CPC ...... A61B 5/0006; A61B 5/04; A61B 5/0412; A61B 5/0402; A61B 5/04525; A61B 5/046
USPC .................................. 600/508, 509, 518, 515
See application file for complete search history.

(56) References Cited

U.S. PATENT DOCUMENTS

| | | | | |
|---|---|---|---|---|
| 5,772,604 A | * | 6/1998 | Langberg et al. | 600/518 |
| 5,868,680 A | * | 2/1999 | Steiner et al. | 600/518 |
| 6,064,906 A | * | 5/2000 | Langberg et al. | 600/518 |

* cited by examiner

*Primary Examiner* — Allen Porter, Jr.
(74) *Attorney, Agent, or Firm* — SV Patent Service

(57) ABSTRACT

A computer-assisted method for quantitative characterization and treatment of ventricular fibrillation includes preprocessing a time series of an atrial fibrillation signal obtained from a patient, segmenting the time series of the AF signal into activation segments by the computer system, obtaining local activation waveforms (LAW) from the activation segments, determining degrees of similarity between the LAWs, and identifying one or more critical regions in the patient's atria if the LAWs have degrees of similarity exceeding a first threshold value.

11 Claims, 16 Drawing Sheets

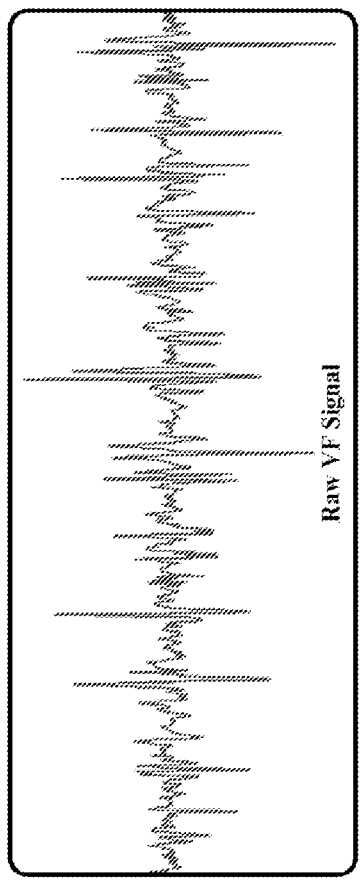 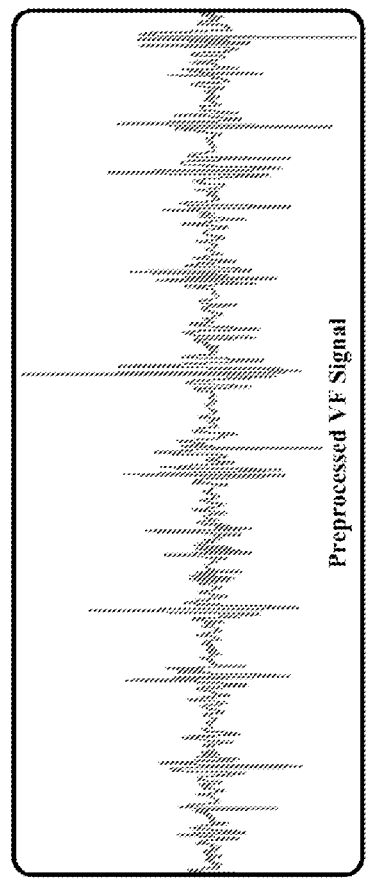
Figure 3A
Figure 3B

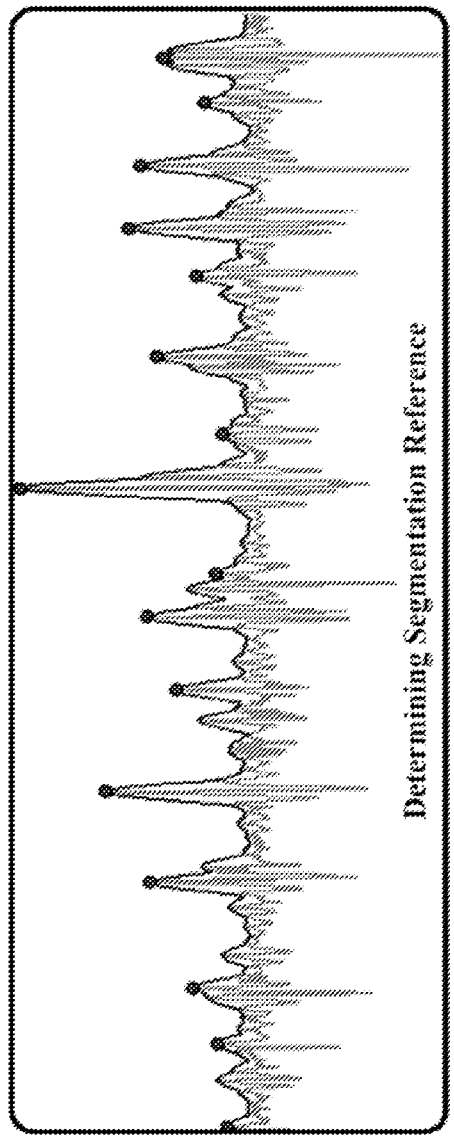
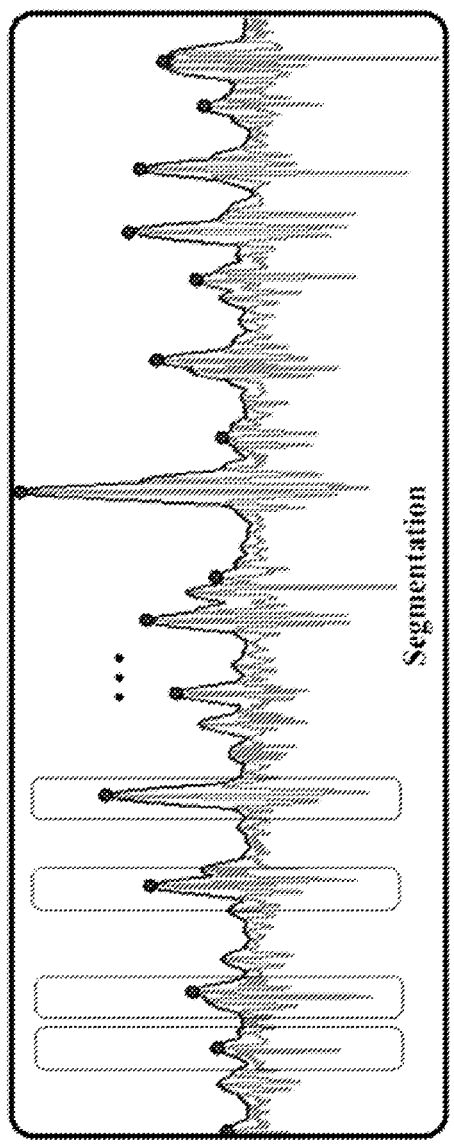
Figure 4D
Figure 4E

SYSTEM AND METHOD FOR IMPROVED COMPLEX FRACTIONATED ELECTROGRAM ABLATION

BACKGROUND OF THE INVENTION

Atrial fibrillation (AF) is the most common type of tachyarrhythmia encountered in clinical practice. Pulmonary vein isolation (PVI) has become the mainstream catheter ablation technique for AF. For persistent AF, substrate modification with complex fractionated electrogram (CFE) ablation is considered to be necessary to patients who have not responded to PVI.

Conventional AF identification methods include dominant frequency (DF) analyses in frequency domain of consecutive electrograms, and CFE mean analysis in time domain of consecutive electrograms. Both methods produce average results based on activation intervals, which not applicable to diagnosing persistent or late stage AF patients. In particular, CFEs are usually observed in many regions of the atria, which make it difficult to identify critical atrial substrate using the conventional AF identification methods.

There is therefore a need to more accurate identification of critical regions and discriminate them from by-standers than conventional AF identification methods.

SUMMARY OF THE INVENTION

The present application discloses an improved method for effectively identifying the substrate nature and localizing critical regions by more accurately analyzing atrial fibrillation signal from a patient. In contrast to conventional techniques that focus on the quantization of fractionality in the AF signals, the presently disclosed method is aimed to discover the repeating patterns among the fractionated AF signals as a way for enhancing the efficacy of catheter ablation and long-term outcome. For persistent AF, substrate modification with complex fractionated electrogram ablation is considered to be necessary in patients who have not responded to PVI. However, CFEs are usually observed in many regions of the atria, making identification of critical atrial substrate difficult. The presently disclosed method can discover regional disparities of the electrogram characteristics between the important CFE and the bystander CFEs which are difficult to identify by the interval analysis, dominant frequency value, and the temporal variation of the DF peaks (bandwidth of the DF peaks or the harmonic index in Fourier spectrum of AF signal). The presently disclosed method can differentiate those sites with repeating patterns from the bystander CFE and thus increase the rate of successful procedural AF terminations and long-term outcome after the first ablation procedure.

In a general aspect, the present invention relates to a computer-assisted method for quantitative characterization and treatment of ventricular fibrillation. The computer-assisted method includes: preprocessing, by a computer system, a time series of an atrial fibrillation (AF) signal obtained from a patient; segmenting the time series of the AF signal into to activation segments by the computer system; obtaining local activation waveforms (LAW) from the activation segments; determining degrees of similarity between the LAWs; and identifying one or more critical regions in the patient's atria if the LAWs have degrees of similarity exceeding a first threshold value.

Implementations of the system may include one or more of the following. The activation segments can be identified based on maximum overlapping of the activation segments. The computer-assisted method can further include normalizing the LAWs in the activation segments before the step of determining degrees of similarity between LAWs. The computer-assisted method can further include calculating distances between different LAWs, wherein the degrees of similarity between LAWs are determined based on the distances between the different LAWs. The distances are calculated between successive LAWs and non-adjacent LAWs. Degree of similarity between two of the LAWs increases as the distance between the two LAWs decreases. The computer-assisted method can further include preprocessing the AF signal by applying order filters to the time series of the AF signal. The computer-assisted method can further include preprocessing the time series of the AF signal by band filtering before the step of applying order filters. The computer-assisted method can further include acquiring a time series of the atrial fibrillation signal from the patient.

In another general aspect, the present invention relates to a computer-assisted method for quantitative characterization and treatment of ventricular fibrillation. The computer-assisted method includes identifying, by a computer system, deflections in a time series of the AF signal obtained from a patient; calculating a mean value of intervals between consecutive deflections in the AF signal; calculating Kurtosis value of a distribution of the intervals between the consecutive deflections in the AF signal; and identifying true complex fractionated electrogram areas if the mean value of the intervals is smaller than a first threshold, and if the Kurtosis value of the distributions of the intervals is larger than a second threshold.

Implementations of the system may include one or more of the following. The computer-assisted method can further include segmenting the time series of the AF signal into the activation segments before the step of obtaining local activation waveforms from the activation segments. The computer-assisted method can further include applying order filters to the time series of the AF signal before the step of segmenting. The computer-assisted method can further include preprocessing the time series of the AF signal by band filtering before the step of applying order filters. The computer-assisted method can further include obtaining local activation waveforms from the time series of the AF signal; determining degrees of similarity between LAWs; and identifying one or more critical regions in the patient's atria if the associated LAWs have degrees of similarity exceeding a third threshold value. The computer-assisted method can further include normalizing the LAWs in the activation segments before the step of determining degrees of similarity between LAWs. The computer-assisted method can further include calculating distances between the LAWs, wherein the degrees of similarity between the LAWs are determined based on the angles between the LAWs. The distances can be calculated between successive LAWs and non-adjacent LAWs. Degree of similarity between two of the LAWs increases as the distance between the two LAWs decreases.

Although the invention has been particularly shown and described with reference to multiple embodiments, it will be understood by persons skilled in the relevant art that various changes in form and details can be made therein without departing from the spirit and scope of the invention.

BRIEF DESCRIPTION OF THE DRAWINGS

The following drawings, which are incorporated in and form a part of the specification, illustrate embodiments of the present invention and, together with the description, serve to explain the principles of the invention.

FIG. 3A illustrates a raw AF signal obtained by the system in FIG. 1.

FIG. 3B illustrates pre-processing of the AF signal.

FIGS. 4A-4E illustrate segmentation of the AF signal.

DETAILED DESCRIPTION OF THE INVENTION

Figure 1:
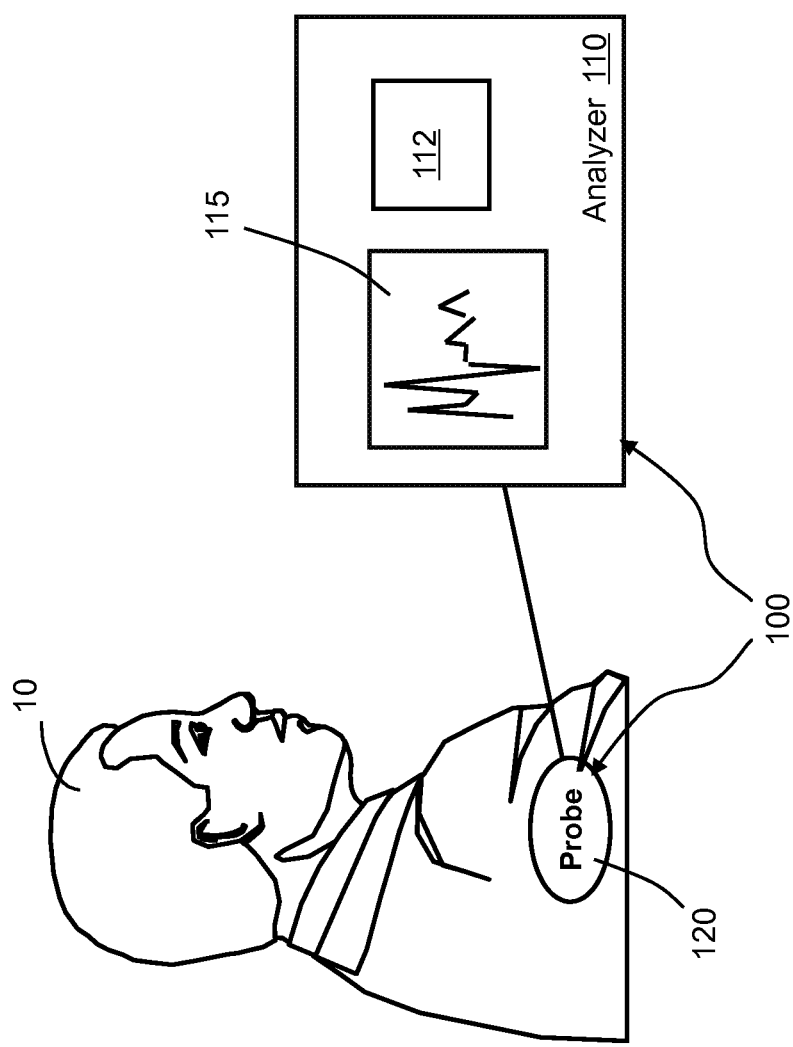
FIG. 1 is a schematic diagram of a system for evaluating atrial fibrillation (AF) in accordance to the present invention.

Referring to FIG. 1, an AF evaluation system 100 includes an analyzer 110 and a probe 120 that can be attached to a patient 10. The probe 120 can include a sensor, a transducer, or an electrode configured to measure intracardiac AF signals from the patient 10. The probe 120 can send the AF signals to the analyzer 110, often in analog form. The analyzer 110 can include an analog-to-digital (A/D) converter for digitizing the AF signals. The analyzer 110 also includes a computer processor 112 that is configured to process and analyze the AF signals after the AF signals are digitized by the A/D converter. A pre-stored algorithm in the analyzer 110 can rapidly analyze the AF signals, and provide guidance to defibrillation treatments, as described in more detail below. The analyzer 110 can also include necessary input/output devices, and a display 115 for displaying the AF signals and the results of the analysis of the AF signals.

Figure 2:
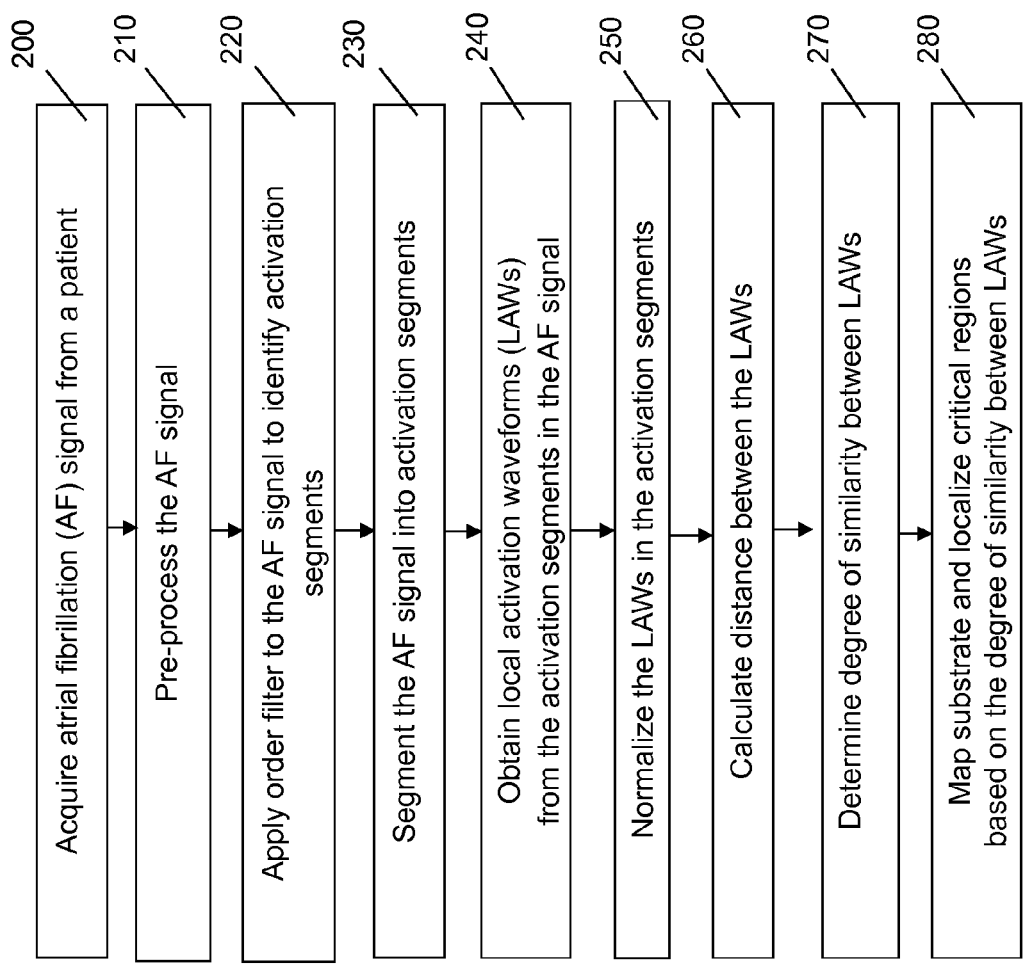
FIG. 2 is a flow diagram for processing and analyzing an atrial fibrillation signal to identify substrate nature and localize critical regions in patient's atria in accordance to the present invention.

In some embodiments, referring to FIG. 2, a process for analyzing a AF signal to identify substrate nature and localize critical regions include one or more of the following steps: a time series of a AF signal, shown in FIG. 3A, is recorded from a patient suffering from atrial fibrillation as described in relation to FIG. 1 above (step 200).

Optionally, the time series of AF signal is preprocessed (step 210). For example, as shown in FIG. 3B, the AF signal can be processed by band filtering to filter out high and low frequency noises.

Figure 4A:
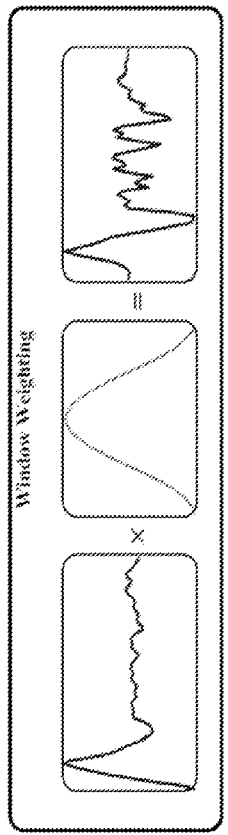
Figure 4B:
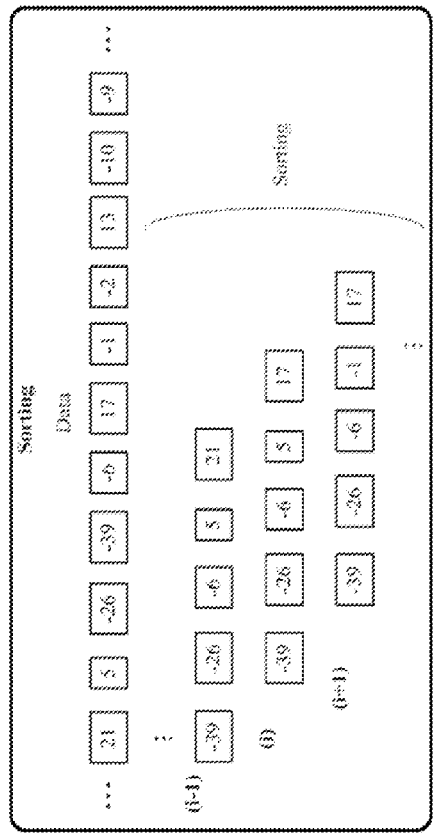
Figure 4C:
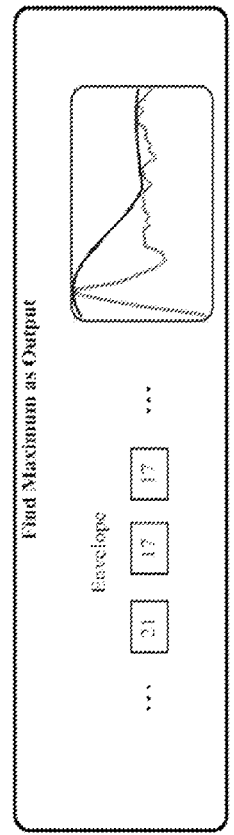

Next, referring to FIGS. 2 and 4A-4E, an order filter is then applied to the time series of AF signal (optionally filtered as described above) to identify activation segments (step 220). The time series of AF signal (the left curve in FIG. 4A) is weighted by a sliding window (the middle curve in FIG. 4A). The largest number among the weighted data (the right curve in FIG. 4A) within each sliding window is obtained as output. The window is shifted forward by 1-point each time and the procedure was repeated for each windowed data until the entire time series of AF signal is analyzed (FIG. 4B). After the envelope is obtained, the local activity peak is determined by finding the points with equal magnitude on the AF signal and envelope (FIG. 4C).

FIG. 4D shows the local activity peaks of the time series of AF signal. The time series of AF signal is segmented into activation segments based on the local activity peaks (FIG. 4E) (step 230). Details about the segmentation of the AF signal are described below in relation to FIG. 8. In some embodiments, the segmented windows in FIG. 4E can have the same widths for the different activation segments. For example, the window width can be set as 55 msec.

Figure 5A:
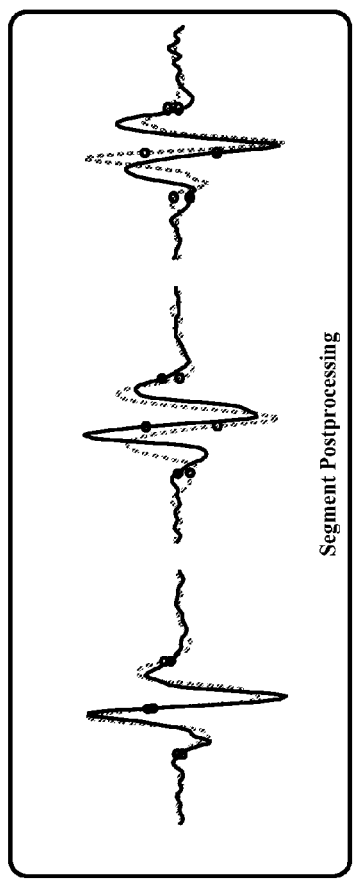
FIG. 5A illustrates local activation waveforms (LAWs) extracted from different segments and the post-processing of the LAWs.

Each segment includes a local activity waveform (LAW). A plurality of LAWs are cut out from the time series of AF signal as shown in FIG. 5A (step 240). The elements of each LAW $x_i$ (composed by m samples) can be regarded as a component of each dimension in a m-dimensional real space, and $x_i$ represented one point in this m-dimensional space.

Figure 5B:
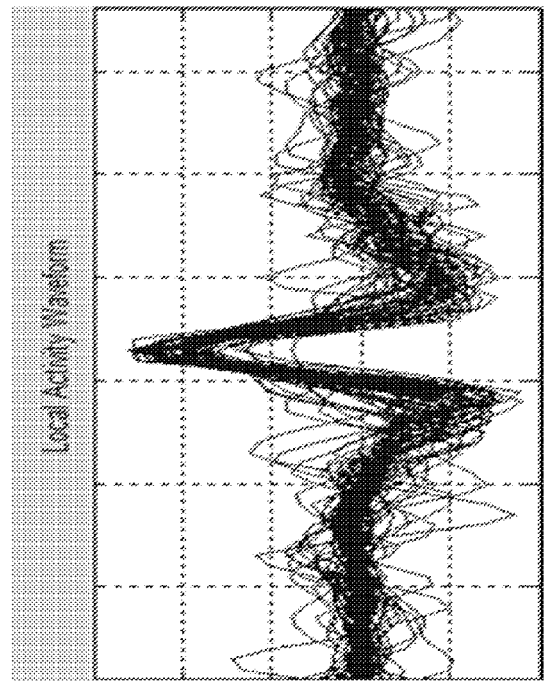
FIG. 5B shows normalized LAWs from different segments.

The segmented AF signal, as shown in FIG. 5A, is normalized (i.e. post-processing) (step 250). The normalized LAWs are shown in FIG. 5B. Each LAW was normalized to eliminate the variation of the amplitude of LAWs. Specifically, the normalization is achieved by dividing the LAW $x_i$ by its standard norm as denoted by $$s_i = \frac{x_i}{\sqrt{\sum_{j=1}^{m} x_{ij}^2}} \quad (1)$$

where $s_i$ is the $i^{th}$ normalized LAW. Similar to the case of $x_i$ representing a point of the m-dimensional real space, the $i^{th}$ normalized LAW $s_i$ represents a point in the m-dimensional unitary sphere.

The distances between every pairs of LAWs (including adjacent and non-adjacent LAWs) were then defined by the standard metric of the sphere as given by $$d(s_i, s_j) = \cos^{-1}(s_i \cdot s_j) \quad (2)$$

where $s_i$ and $s_j$ represent the $i^{th}$ and $j^{th}$ normalized LAW and (·) denotes the scalar product. The distances between LAWs shown in FIG. 5B are calculated (step 260).

Figure 6A:
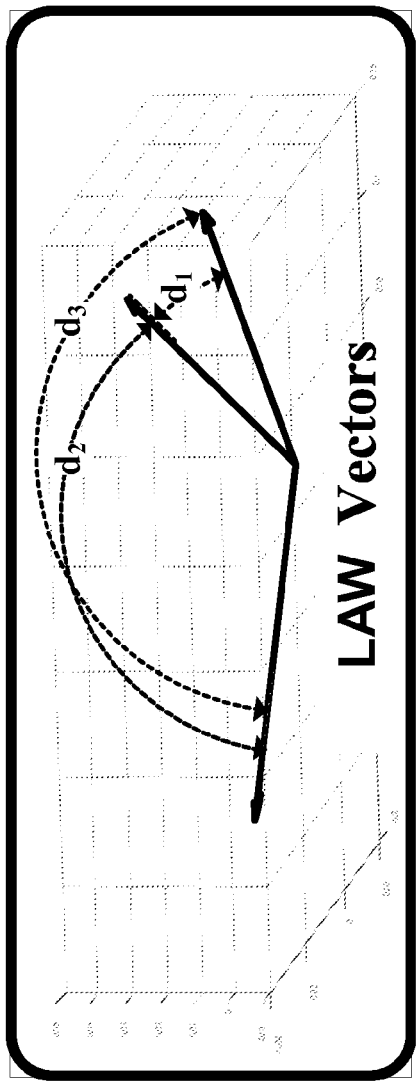
FIG. 6A shows angles between different pairs of LAW vectors.

LAW vectors are constructed as illustrated in FIG. 6A. A similarity index (ρ) is then calculated based on the angles between LAW vectors (i.e. the distance between the associated LAWs). The similarity index (ρ) is inversely proportional to angle between LAW vectors (and to the distance between the associated LAWs). If the angle between LAW vectors of a pair of LAWs is smaller than a pre-determined threshold, this LAW pair is regarded as similar, and vice versa.

The similarity index $\rho(\epsilon)$ is defined as the ratio of the number of similar LAW pairs to the total number of LAW pairs in the analyzed recording $$\rho(\varepsilon) = \frac{2}{N(N-1)} \sum_{i=1}^{N} \sum_{j=i+1}^{N} \Theta(\varepsilon - d(s_i \cdot s_j)) \quad (3)$$

$$\Theta(x) = \begin{cases} 1, \forall x > 0 \\ 0, \forall x \le 0 \end{cases}$$

Figure 6B:
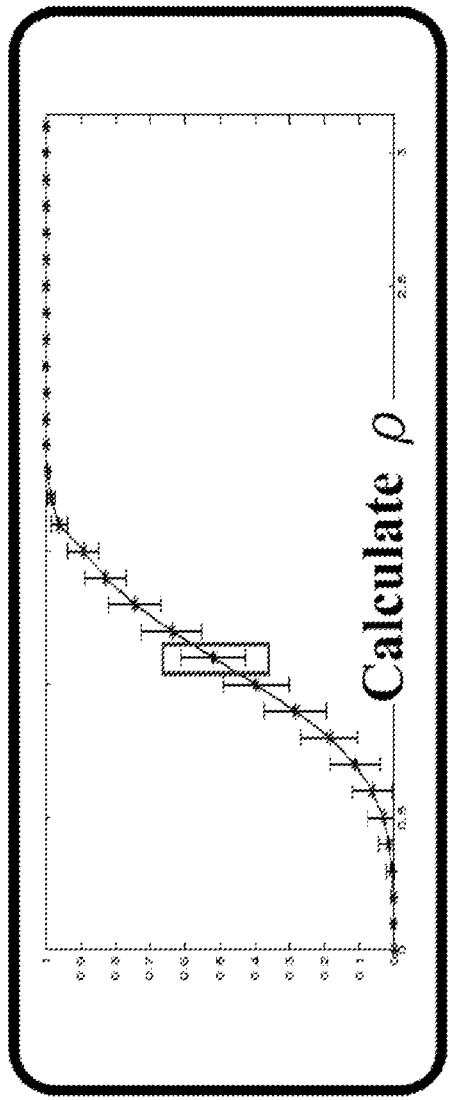
FIG. 6B shows cumulative distribution of similarity index (ρ) based on the angles between the LAW vectors and an optimal threshold in the cumulative distribution of the similarity index for determining termination sites within the continuous CFEs.

In Equation (3), the parameter $\epsilon$ is an adjustable threshold. By comparing the distance between two LAWs derived in (2) to the threshold distance $\epsilon$, we determined these two LAWs to be similar if the distance d was less than $\epsilon$, or dissimilar if d was greater than or equal to $\epsilon$. A concept illustration of the 3D case (i.e., m=3) is given in FIG. 6B which shows a cumulative distribution of similarity index (ρ). An optimal threshold $\epsilon$ can be determined in the cumulative distribution of similarity index (ρ) to determine degree of similarity between LAWs as (step 270). LAWs higher than the threshold in the cumulative distribution of similarity index (ρ) are considered as resembling each other.

For a given $\epsilon$, the index $\rho(\epsilon)$ in (3) can be regarded to indicate the probability of finding similar LAW pairs in the analyzed AF electrogram. Although the values of the pre-defined parameters (e.g. $\epsilon$ and m, respectively representing the threshold distance and window length of LAWs) may alter the results of ρ, the values of ρ were similar within certain ranges of the values of pre-defined parameters by using peak alignment and for the best discriminative performance. In one non-limiting example, the window length of LAWs and $\epsilon$ are set to 50 msec and 1.1 respectively.

The resembling LAWs are mapped into substrate, as shown in FIGS. 7A-7D, which identifies critical regions (step 280). In the present application, the term substrate means the cardiomyocytes located in the region-of-interested of atria. Modification often means the ablation procedure perform on the substrate.

Figure 7A:
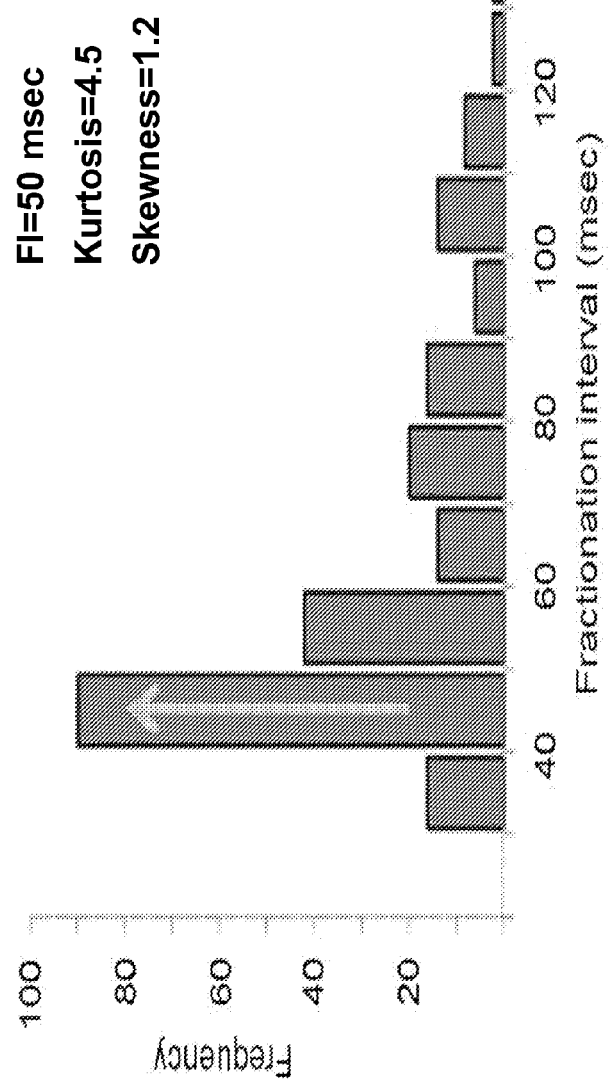
FIGS. 7A and 7B show histogram analysis of fractionation interval over 6 seconds at an AF termination site.
Figure 7B:
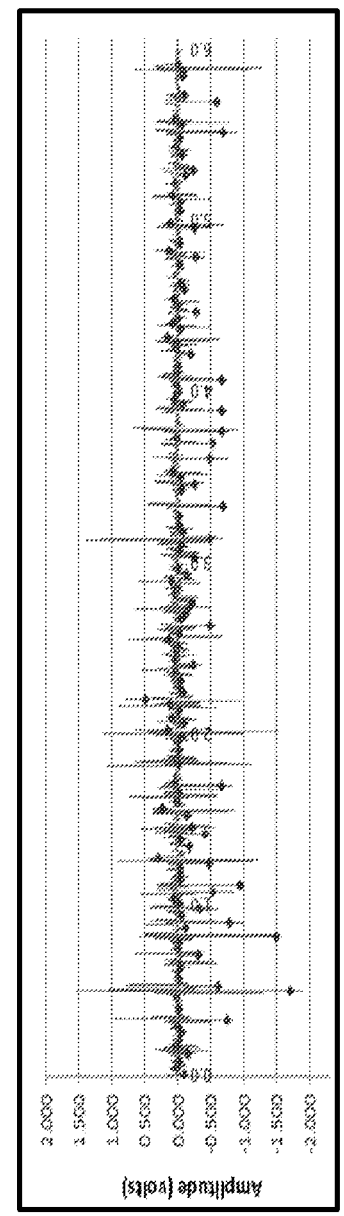
Figure 7C:
FIGS. 7C and 7D show histogram analysis of fractionation interval over 6 seconds at a continuous CFE site.
Figure 7D:
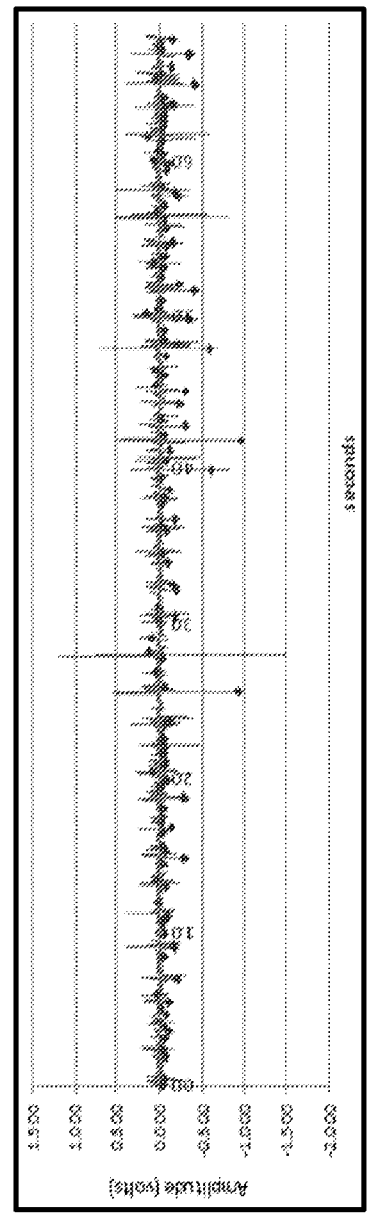

FIGS. 7B and 7D demonstrate the AF electrograms recorded from two different sites and the corresponding distribution of deflection intervals.

FIGS. 7A and 7B respectively show histogram and fractionation interval over 6 seconds at an AF termination site. The histogram (FIG. 7A) at this site exhibits a high kurtosis (of 4.5) with a sharp peaked distribution and positive skewness. This site exhibited a continuous fractionated signal of 50 msec.

FIG. 7C and 7D show histogram analysis and fractionation interval over 6 seconds at a continuous CFE site. The histogram (FIG. 7C) at this site exhibits a low kurtosis (of 2.1) and positive skewness, whereas this site exhibits a continuous fractionated signal of 53 msec. CFE-targeted ablation at that site did not terminate AF.

Although mean values of the distribution of interval deflections for the two sites described above are similar (50 msec vs. 53 msec), but their Kurtosis values are quite different (4.5 vs. 2.1). It is discovered in the present invention that that the ablation on the site with high kurtosis can terminate the AF.

As described above, for longer duration AF, substrate modification with a complex fractionated electrogram ablation is considered to be necessary in patients who do not respond to PVI. The development of automated analysis algorithms for electrogram fractionation is important for a reproducible and objective assessment of this technique. However, most of the algorithms have been based on the mean fractionation interval (FI) between the deflection of the time-domain electrograms, such as the CFE-mean of the NavX system or shortest complex interval of the CARTO system. Detection is based on 3 criteria, set by the user, in which the deflection must: (1) exceed an adaptive peak-to-peak sensitivity threshold that is set at a reference-amplitude slightly greater than the baseline noise; (2) possess a downstroke morphology for which the leading maximum and trailing minimum amplitudes occur within a time duration that is set to minimize the detection of broad, far-field events; and (3) exceed a refractory period after the previous detection that is set to minimize multiple detections on a single deflection event. The variation in the FIs acquiring by those modalities may be important for the interpretation of the substrate characteristics. Therefore, if the local FIs are not normally distributed, there is a limitation of the mean FI with a clinical application due to the temporal variation.

The present application discloses that the temporal variation in the annotated FI can provide important information to determine the features of critical CFEs in addition to the conventional FI algorithm. i.e., the local consistency of the fractionated electrograms can be assessed according to the distribution of FIs for a recording duration. The assessed electrograms in each patient were acquired and characterized by the "kurtosis" of the FI distribution. Briefly summarized, kurtosis measures the shape of distribution of the fractionated intervals within the window beyond simply using their mean or standard deviation. The value of kurtosis gives the relationship between each of the FIs to their mean. The higher the value of kurtosis, the less probable that FIs deviate from their mean.

Figure 8:
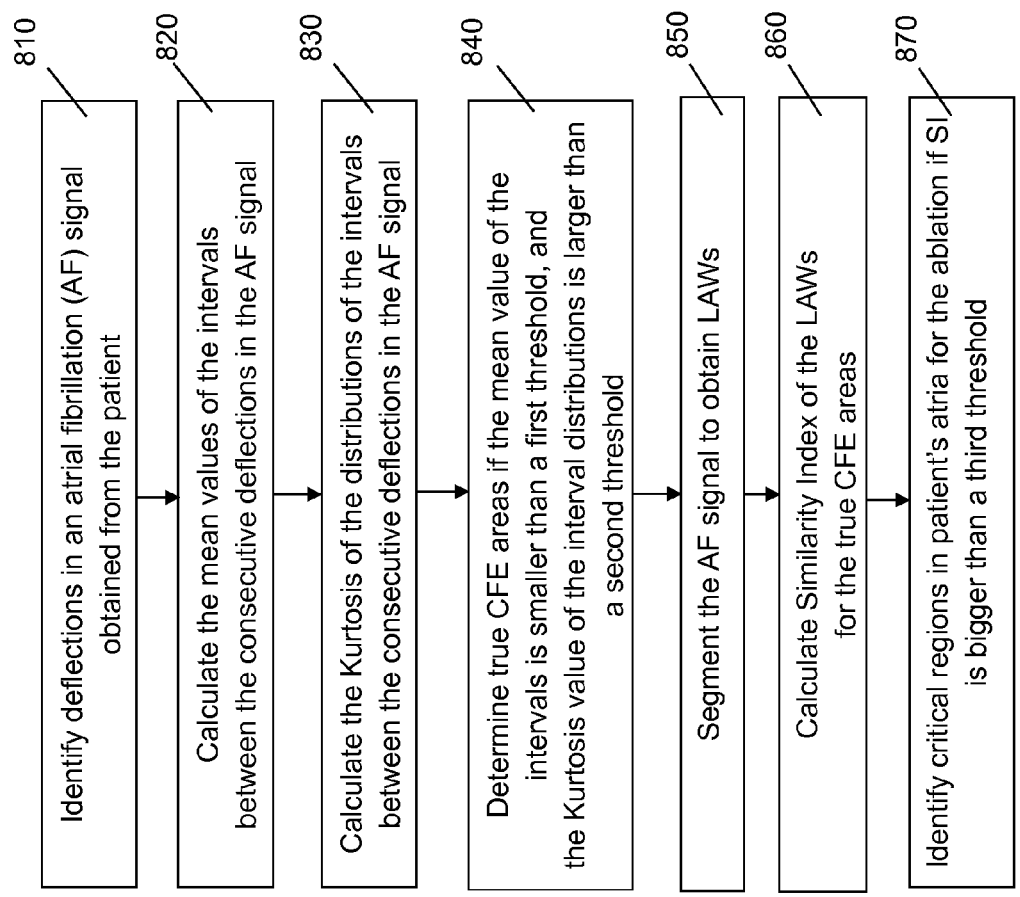
FIG. 8 is a flow diagram showing detailed steps of segmenting an atrial fibrillation signal to identify critical regions in patient's atria in accordance to the present invention.

In some embodiments, referring to FIG. 8, the presently disclosed method identifies critical regions (i.e. the "crucial" or "true" CFE) and discriminates them from by-standers by one or more of the following detailed steps: deflections in an AF signal are identified (step 810). The intervals between the consecutive deflections are calculated. The mean value of the intervals is calculated (step 820). The Kurtosis of the interval distributions is calculated (step 830). True CFE areas for the ablation are determined based on the criteria: mean value of the intervals is smaller than a first threshold, and the Kurtosis value of the interval distributions is larger than a second threshold (step 840).

In some embodiments, the operation accuracy can be further improved by segmentation steps as described in FIG. 2. The time series of the AF signal can be segmented into activation segments to obtain LAWs, as described above (step 850). Similarity index between LAWs is calculated for the areas identified (step 860). The critical regions in the patient's atria for the ablation are identified if SI is bigger than a third threshold (step 870).

If the areas which are identified as the true CFE are still extensive, the present disclosed method further identifies critical regions and discriminate them from by-standers, the presently disclosed method evaluates characteristics of a region by more accurately analyzing AF signal including: an elaborative segmentation to the AF signal and quantitative assessment of the repeating patterns in AF signal.

Mechanistic Considerations

The above described process is based on the following mechanistic considerations: Previous studies demonstrated the efficacy of adjunctive CFE ablation in addition to circumferential PVI. Considering that CFEs may play an active role in persistent AF, a CFE that maintains AF should be continuous and stable over time. Based on the time-domain signal, catheter ablation at sites displaying a greater percentage of continuous activity was associated with slowing or procedural AF termination (successful stop of AF) by catheter ablation in chronic AF. In recent years, automatic algorithms for 3D mapping systems have provided a rigorous quantitative analysis enabling the identification of the continuous CFEs and stability of the CFE distribution over time.

Mathematically, the morphological change over the distribution of the deflection types, total duration of the discrete electrograms, and intervals between consecutive deflections within the segmented windows, all contributed to the measurement of the stationarity feature of the electrograms. To non-paroxysmal AF patients, it is important to differentiate the culprit CFEs from the bystander CFEs. The stability of the electrograms may also reflect the presence of a focal pattern of activation.

Assuming consistent wavefront dynamic and activation patterns are emanating from the AF sources, repetitive waveforms of similar electrogram morphology should appear near the potential AF maintainers. A higher level of the electrogram similarity index over time at the continuous CFEs was more likely to respond to substrate modification. This can provides an alternative mapping tool to guide substrate modification.

Validation

One hundred consecutive persistent AF patients that received catheter ablation have been studied using the method described above. A total of 9558 fibrillatory electrograms were analyzed in this study (139±30 sites per patient in LA).

Substrate Mapping of the Global Atria

Figure 9A:
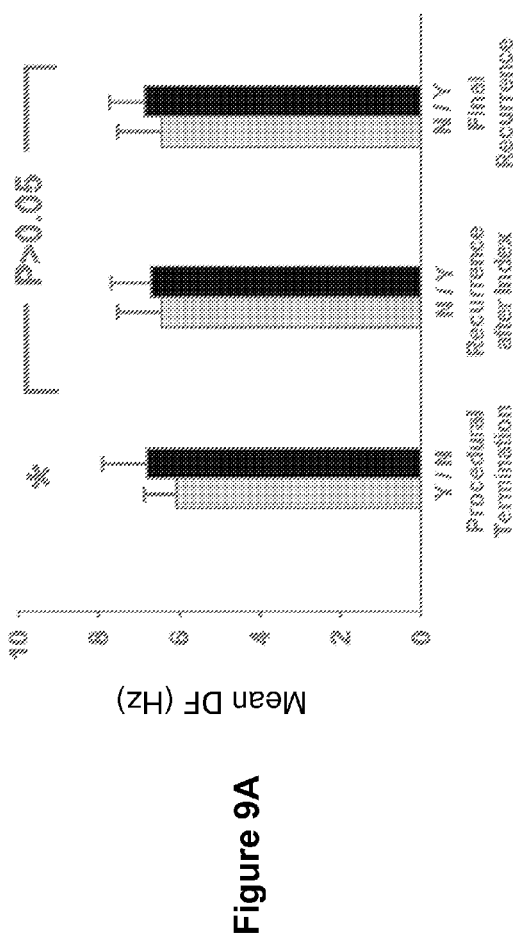
FIG. 9A shows the use of mean dominant frequency of the left atrium for predicting AF procedural termination, recurrence after the first ablation procedure, and recurrence after the final procedure.

FIG. 9A shows mean dominant frequency of the left atrium for predicting AF procedural termination, recurrence after the first ablation procedure, and recurrence after the final procedure. The phrase "procedure termination" means successfully stop the AF by catheter ablation. The phrase "recurrence after index" means the AF occurs again in some specific duration (e.g., in a month or half year). The phrase "final recurrence" means although AF disappears during the duration above, it occurs finally.

Figure 9B:
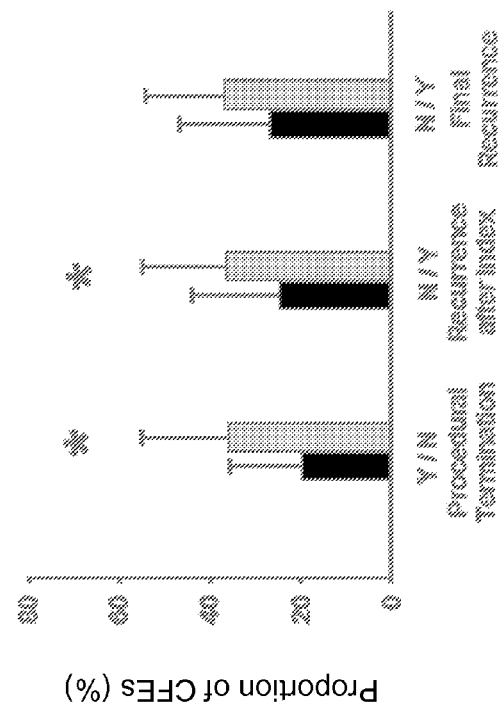
FIG. 9B shows the use of proportion of the continuous CFEs of the left atrium for predicting AF procedural termination, recurrence after the first ablation procedure, and recurrence after the final procedure.

FIG. 9B shows proportion of the continuous CFEs of the left atrium for predicting AF procedural termination, recurrence after the first ablation procedure, and recurrence after the final procedure. In FIGS. 8A and 8B, the * symbol means the discriminant performance is successful and reliable. "Y" and "N" respectively mean "True" and "False".

FIGS. 9A and 9B show comparisons of electrogram characteristics of the entire left atrium in the patients who did and did not respond to CFE ablation in terms of procedural AF termination and long-term AF recurrence (efficacy of single and multiple procedures without drugs). Patients with atrial substrate characteristics harboring rapid activity and more fractionated electrograms are less likely to respond to CFE ablation, as indicated by a higher DF (dominant frequency) ($P>0.05$), and higher proportion of CFEs in the left atrium ($P<0.01$), wherein the p-value is defined as the probability of obtaining a test statistic at least as extreme as the one that was actually observed.

To identify possible target of ablation, previous studies used the dominant frequency (DF) and the location with highest DF as the target. However, FIG. 9A shows that for all the recurrence patients, DF value (The "first generation method") has a P-value larger than 0.05 and is no longer effective for discrimination.

FIG. 9B illustrates the proportion of continuous CFE can be a better index for discriminating/predicting the results, whether the P-value is larger than 0.05 or not is critical. FIG. 9B also shows that continuous CFE (the "second generation method") is somehow effective since the proportion of continuous CFE become higher on persistent patients, but we obviously cannot ablate all the substrate with continuous CFE. So there is a need for an improved method to better identify the ablating target.

Correlation of Ablation Outcome and Electrogram Characteristics

Figure 10A:
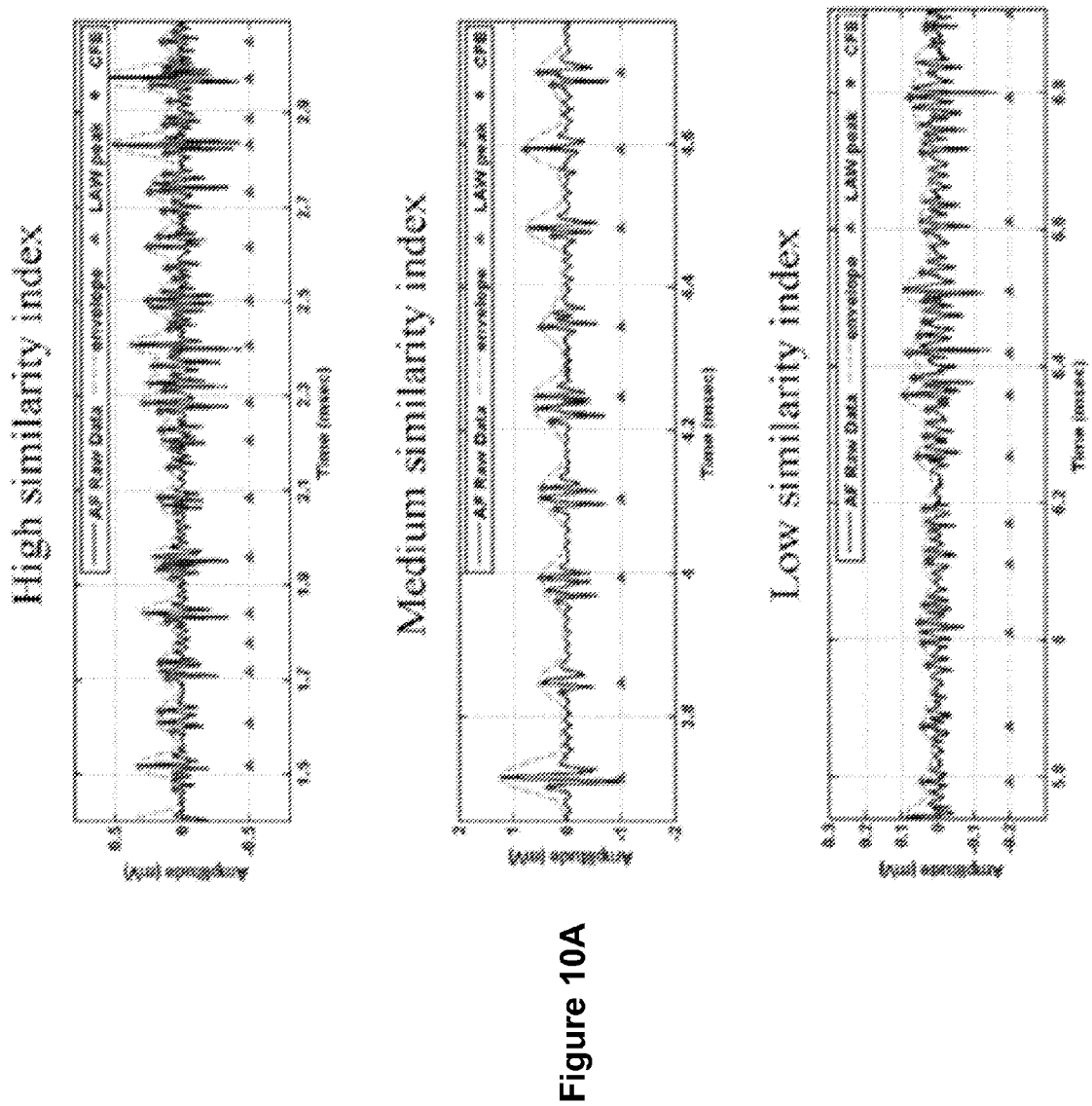
FIG. 10A show continuous complex fractionated electrograms having different similarity indices.
Figure 10B:
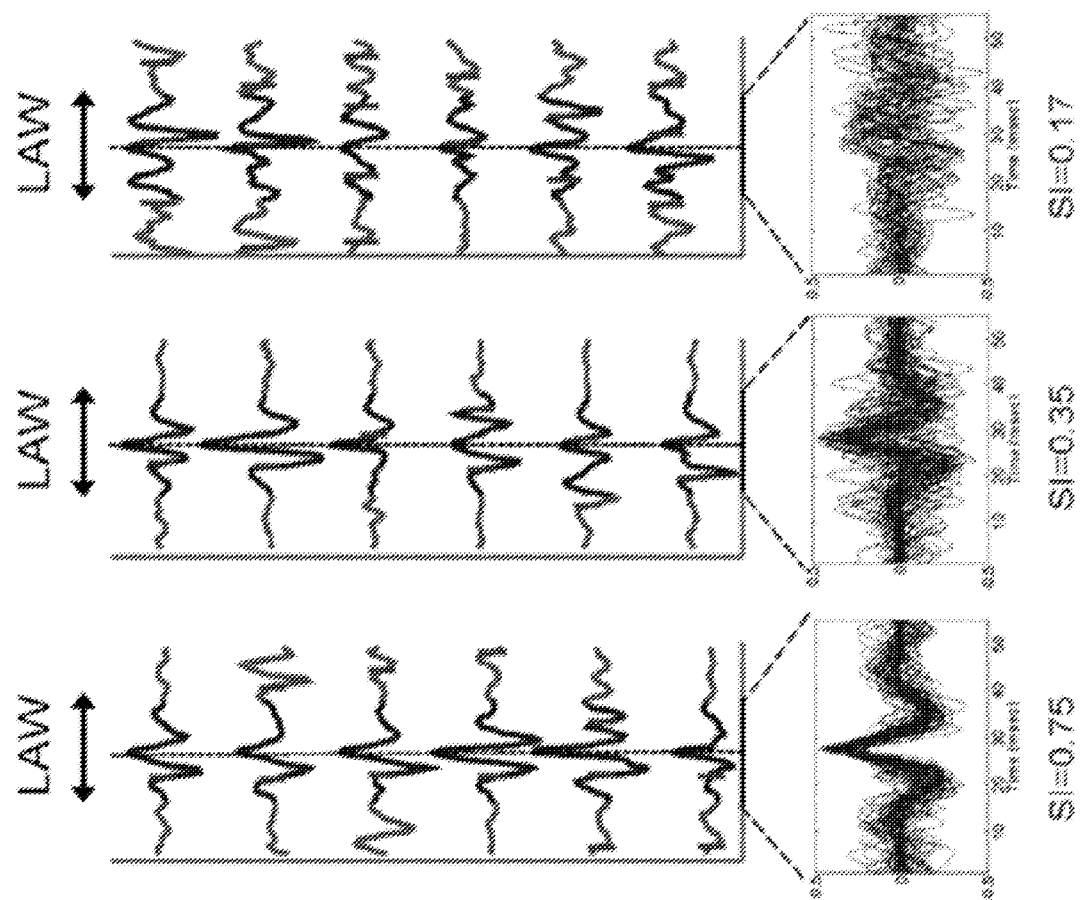
FIG. 10B shows LAWs respectively obtained from the complex fractionated electrograms in FIG. 10A.

FIGS. 10A and 10B show analysis of the electrogram similarity with different types of continuous complex fractionated electrograms (CFE). FIG. 10A shows exemplified bipolar fractionated electrograms including rapid activity and continuous electrograms with high, medium and low similarity indices. The envelop function of the filtered data (dotted line) and start points of the CFE deflections (triangle) are shown. Each LAW consists of multiple deflections and some of those might be CFE deflections. FIG. 10B shows LAWs obtained from the electrograms with high, medium and low similarity indices in FIG. 10A. The normalized electrograms of all the LAWs overlap with their center peaks and corresponding similarity index. Note that in addition to the high morphological similarity of the LAWs in the high similarity site, the CFE deflections (triangle label) are temporally well aligned.

The averaged similarity index of the targeted CFEs was higher in terms of procedural termination and AF recurrence. A disparity of the similarity was not observed in the non-continuous CFEs (0.51±0.09 vs. 0.51±0.11, P=NS) and non-CFEs (0.41±0.13 vs. 0.44±0.11, P=NS, in the patients with and without termination, respectively.

In patients with procedural termination, the termination sites (N=27) were characterized by a significantly higher similarity index compared to the other ablation sites (0.65±0.086 vs. 0.56±0.076, P=0.0001).

Figure 11A:
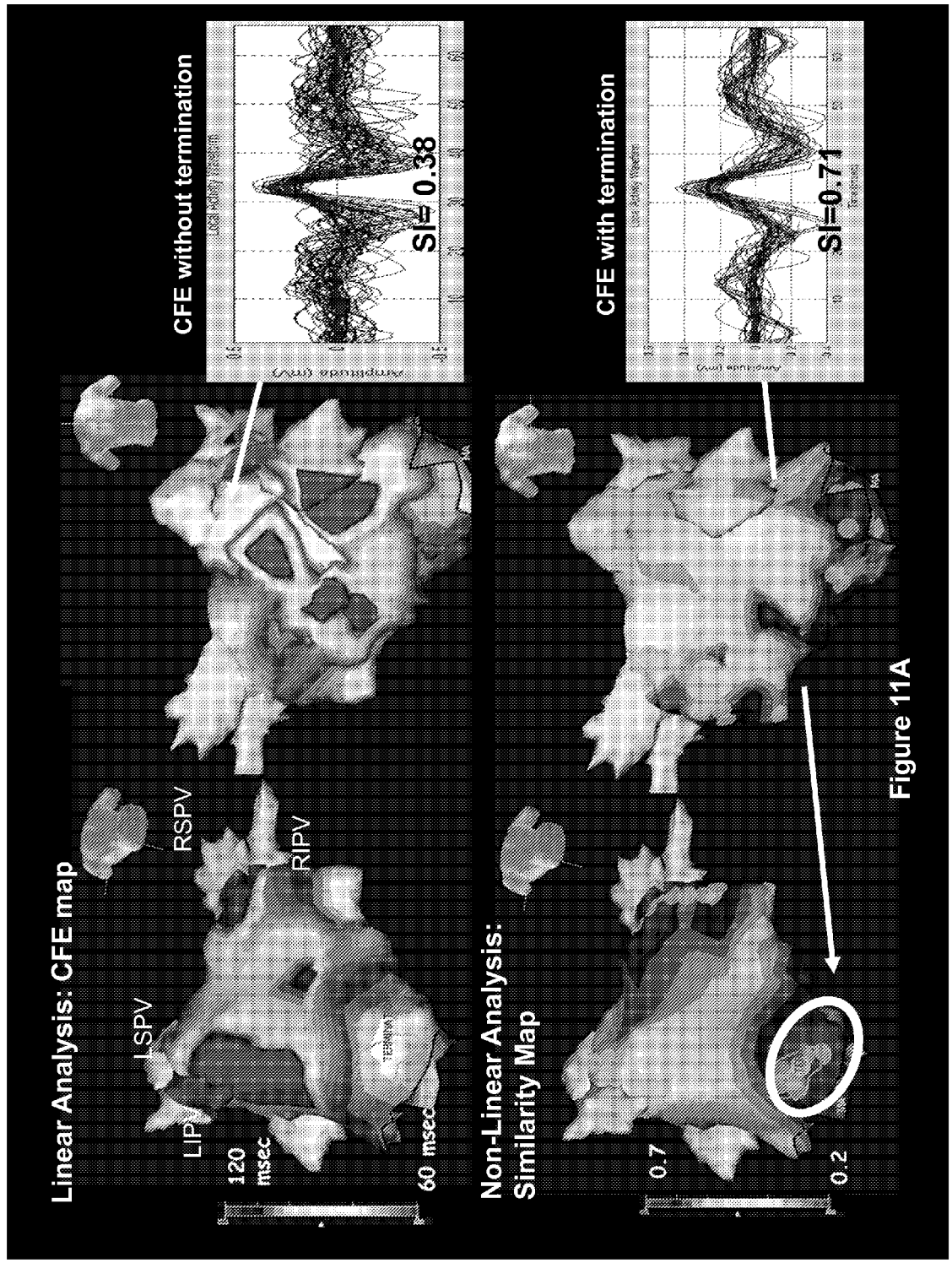
FIG. 11A shows exemplified 3D similarity map and fractionation map in patients with procedural AF termination.
Figure 11B:
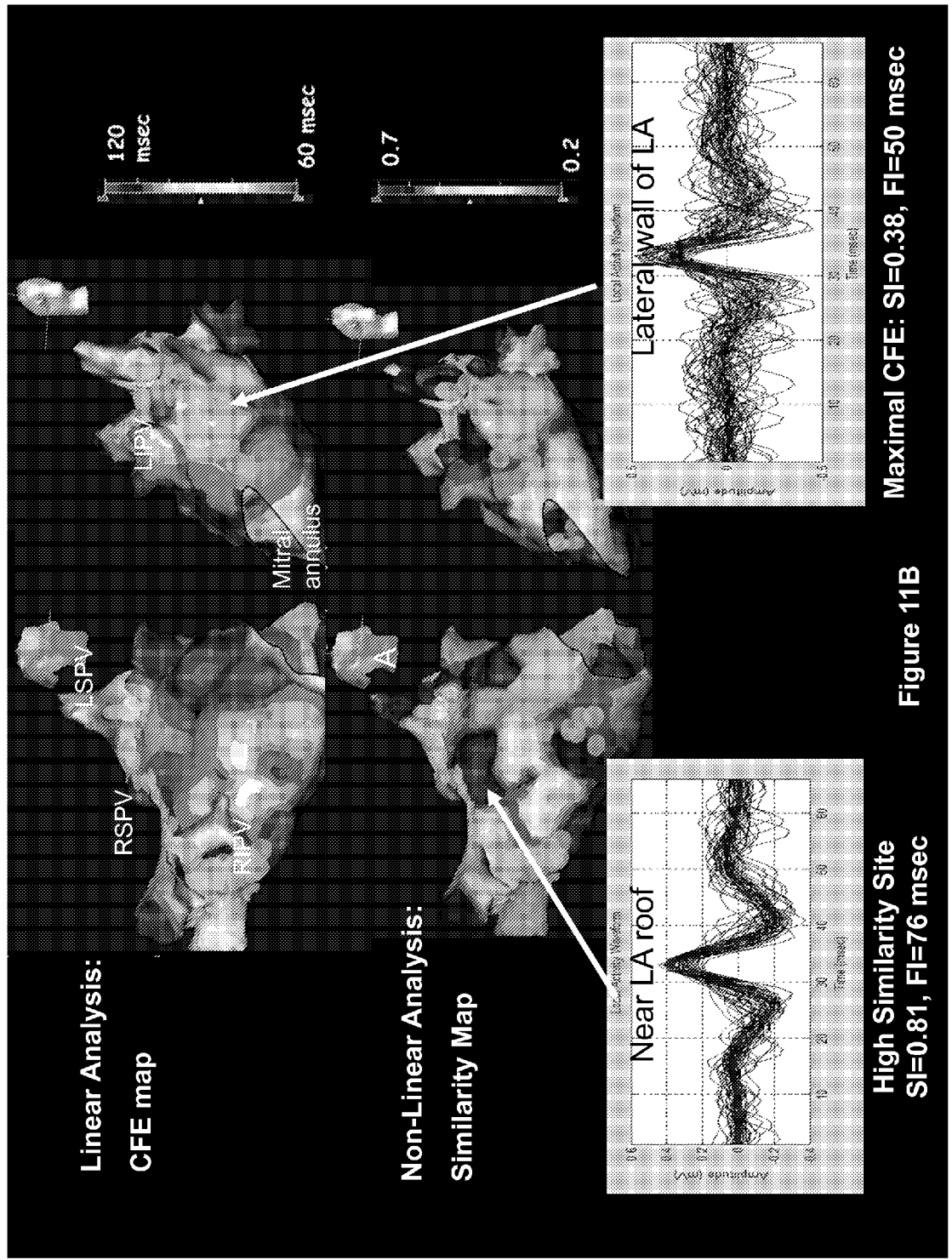
FIG. 11B shows exemplified 3D similarity map and fractionation map in patients without procedural AF termination.

FIGS. 11A and 11B show examples of 3D similarity map and fractionation map in a patient with and a patient without procedural AF termination. FIG. 11A shows an example of procedural AF termination at the posterolateral LA, where the high level of SI was compatible with the maximal CFEs. In contrast, in FIG. 11B, maximal CFE ablation in the lateral mitral annulus and LA septum could not terminate AF. Subsequent roof line ablation (with a mean FI of 76 msec, SI=0.81) terminated AF without AF recurrence during long-term follow-up.

In FIG. 11A, the maximal fractionated sites were identified with the high similarity index in the lateral mitral isthmus region. The similarity index locally was 0.71, whereas the similarity index of the CFEs in the anterior wall was 0.38. In contrast, in FIG. 11B, the maximal CFE ablation in the lateral mitral annulus and LA septum could not terminate AF. The maximal CFE was not associated with the high similarity index. The highest similarity near the border of the continuous CFEs was identified in the roof region. In this patient, ablation in the roof region terminated the AF with final SR maintenance during the long-term follow-up. A subsequent roof line ablation (with a mean fibrillation interval of 76 milliseconds, SI=0.81) terminated AF without any AF recurrence during the long-term follow-up.

The Optimal Detection Algorithm for CFEs

Within all the CFE regions (FI<120 msec), a univariate analysis showed that both a shorter mean FI and higher SI were associated with procedural AF termination. The DF value, HI value, and electrogram voltage did not correlate with the termination (P>0.05). A multivariate regression analysis showed that only a higher SI (≥0.57, Odd ratio=4.9, 95%, the confidence interval CI=1.33-18.0, P=0.017) predicted procedural AF termination. Sites with a shorter mean FI did not predict procedural termination (<70 msec, odd ratio=1.69, 95% CI=0.61-4.67, P=0.31).

Figure 12A:
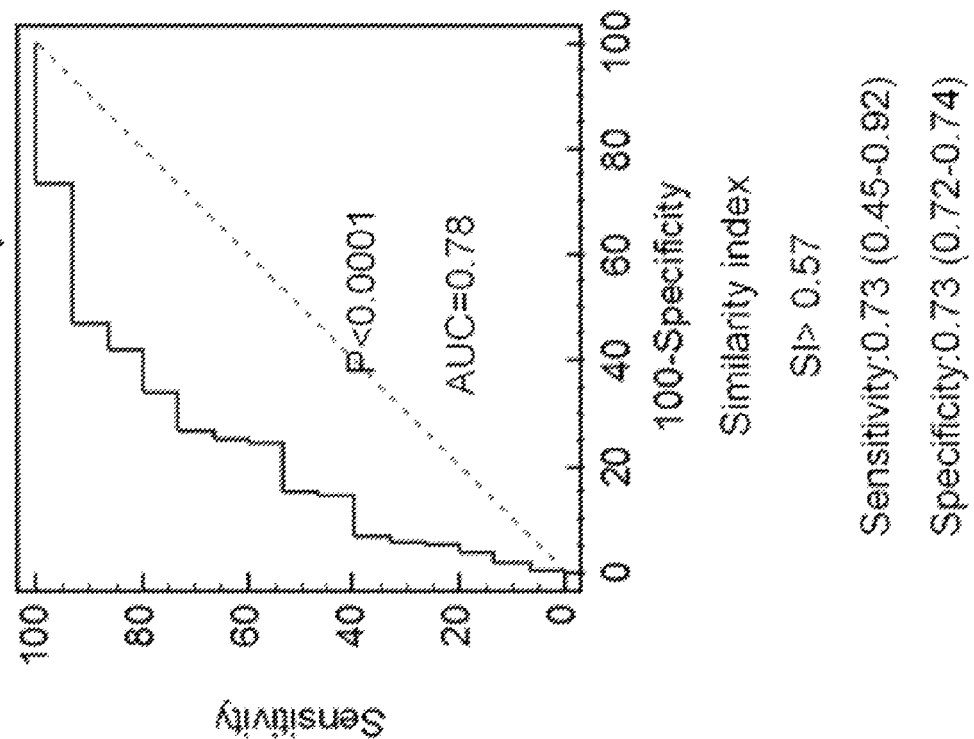
FIG. 12A is a plot of a receiver operating characteristic (ROC) curve showing a optimal threshold in detecting the termination sites within the continuous CFEs based on the algorithm of dominant frequency value.

We analyzed the predictors of the signal characteristics from the procedural termination sites (N=27), and non-terminating ablation sites in patients with and without procedural AF termination (N=7438). FIG. 12A is a plot of a receiver operating characteristic (ROC) curve showing the optimal thresholds in detecting the termination sites within the continuous CFEs based on the algorithm of dominant frequency (DF) value. The ROC curve analysis shows an optimal cut-off threshold value of the DF>10.2 Hz within the continuous CFEs correlated with the termination with a sensitivity of 0.35 (0.12-0.62) and specificity of 0.93 (5% CI=0.90-0.94).

Figure 12B:
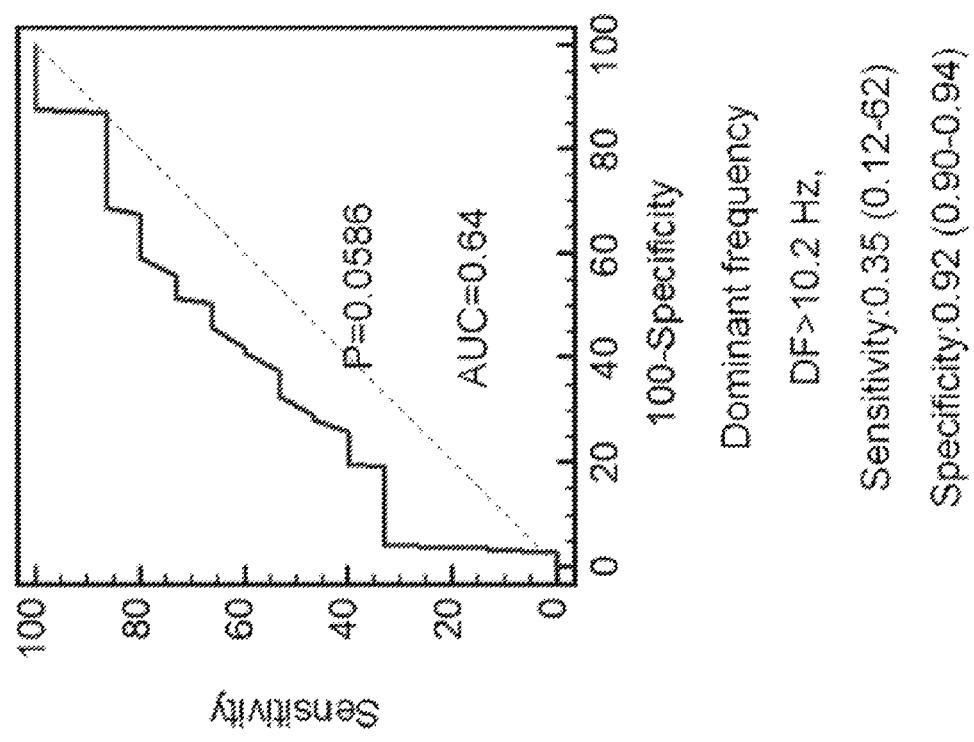
FIG. 12B is a plot of a ROC curve showing optimal threshold in detecting the termination sites within the continuous CFEs based on the algorithm of the similarity index.

FIG. 12B is a ROC curve showing the optimal threshold for detecting termination sites within the continuous CFEs based on the algorithm of the similarity index. This ROC curve analysis shows an optimal cut-off threshold value of the SI≥0.565 within the continuous CFEs correlated with the termination with a sensitivity of 0.73 (95% CI=0.45-0.92) and specificity of 0.73 (5% CI=0.72-0.74, area under curve=0.781, P<0.001).

On the contrary, using the higher DF value to predict the termination sites was difficult (Cut-off value=10.2 Hz, sensitivity of 0.33 (0.12-0.62), specificity=0.95-0.96, area under curve=0.64, P=0.0586, as shown in FIG. 11A). Thus the disclosed CFE method is a much better predictor than DF for termination site predictions.

The disclosed system and methods can include one or more of the following advantages: within the continuous CFEs, a conventional linear signal analysis could not differentiate the termination sites from non-termination sites. The sites with a high level of fibrillation electrogram repetitiveness at the CFEs are important for AF maintenance. The proposed analysis rules 1) proper segmentation and 2) stationarity evaluation to the consecutive fibrillation electrograms can serve as an effective tool for distinguishing the culprit CFEs from the bystander CFEs in patients with persistent AF, and further refine the current substrate modification procedure.

It should be understood that the above described systems and methods are compatible with different configurations and variations without deviating from the spirit of the present invention. For example, AF signals are not limited to surface ECG waveforms.

What is claimed is:

1. A computer-assisted method for quantitative characterization, comprising:
   preprocessing, by a computer system, a time series of an atrial fibrillation (AF) signal obtained from a patient;
   segmenting the time series of the AF signal into activation segments by the computer system, wherein the activation segments are sequential in the time series of the AF signal;
   obtaining local activation waveforms (LAW) from the activation segments that are sequential in the time series of the AF signal;
   determining degrees of similarity between the LAWs obtained from the time series of the AF signal, wherein the step of determining degrees of similarity between the LAWs comprises:
      representing each one of the LAWs by a vector based on strengths of the AF signal at a plurality of sampling points in a respective one of the LAWs; and
      computing a distance between vectors of a pair of LAWs obtained from the same time series of the AF signal to determine degrees of similarity between the pair of LAWs;
   identifying one or more critical regions in the patient's atria if the LAWs obtained from the time series of the AF signal have degrees of similarity exceeding a first threshold value; and
   characterizing atrial fibrillation in the patient based on the one or more critical regions identified in the patient's atria.

2. The computer-assisted method of claim 1, wherein the activation segments are identified at least in part based on overlapping of local maxima in the time series of the AF signal.

3. The computer-assisted method of claim 1, further comprising:
   normalizing the LAWs in the activation segments before the step of determining degrees of similarity between LAWs.

4. The computer-assisted method of claim 1, wherein the distances between vectors of a pair of LAWs are calculated between successive LAWs or between non-adjacent LAWs.

5. The computer-assisted method of claim 1, wherein degrees of similarity between the pair of the LAWs increases as the distance between the pair of LAWs decreases.

6. The computer-assisted method of claim 1, further comprising:
   preprocessing the AF signal by applying order filters to the time series of the AF signal.

7. The computer-assisted method of claim 6, further comprising:
   preprocessing the time series of the AF signal by band filtering before the step of applying order filters.

8. The computer-assisted method of claim 1, further comprising:
   treating atrial fibrillation in the patient based at least in part on the one or more critical regions identified in the patient's atria.

9. The computer-assisted method of claim 1, further comprising:
   calculating a similarity index between multiple pairs of LAWs obtained from the same time series of the AF signal using distances between each of the multiple pairs of LAWs in the same time series of the AF signal.

10. The computer-assisted method of claim 9, wherein the multiple pairs of LAWs are all the LAWs in the same time series of the AF signal.

11. The computer-assisted method of claim 1, wherein the step of computing a distance between vectors of a pair of LAWs obtained from the same time series of the AF signal is computed comprises computing a scalar product of the vectors of the pair of LAWs.

* * * * *